United States Patent [19]

Nesvadba

[11] Patent Number: 5,240,622

[45] Date of Patent: Aug. 31, 1993

[54] DIOXAPHOSPHORINANE COMPOUNDS AS STABILIZERS FOR ORGANIC MATERIALS

[75] Inventor: Peter Nesvadba, Marly, Switzerland

[73] Assignee: Ciba-Geigy Corporation, Ardsley, N.Y.

[21] Appl. No.: 719,859

[22] Filed: Jun. 24, 1991

[30] Foreign Application Priority Data

Jun. 26, 1990 [CH] Switzerland ............... 2126/90-6

[51] Int. Cl.$^5$ ............... C10M 137/12; C10M 137/16
[52] U.S. Cl. ............... 252/32.5; 252/49.8; 252/49.9; 252/400.21; 524/117
[58] Field of Search ............... 252/32.7 E, 49.9, 400.21, 252/32.5, 49.8; 524/117

[56] References Cited

U.S. PATENT DOCUMENTS

| | | |
|---|---|---|
| 2,984,551 | 5/1961 | Scanley et al. |
| 2,984,683 | 5/1961 | Buckler |
| 3,005,020 | 10/1961 | Buckler |
| 3,328,319 | 6/1967 | Galinke et al. |
| 3,388,105 | 6/1968 | Danielisz et al. |
| 3,686,367 | 8/1972 | Cowling ............... 252/400.2 |
| 4,374,219 | 2/1983 | Spivack et al. ............... 252/400.21 |
| 4,507,416 | 3/1985 | Chaser ............... 252/400.21 |
| 4,808,645 | 2/1989 | Ravichandran et al. ....... 252/400.21 |

FOREIGN PATENT DOCUMENTS

1244020 9/1960 France.
902802 8/1962 United Kingdom.

OTHER PUBLICATIONS

Chem. Abst. 96, 122900w (1982).
Chem. Abst. 100, 121212n (1984).
B. A. Arbuzov et al., Bull. Acad. Sci. USSR Div. Chem. 30, 2336 (1982).
B. A. Arbuzov, et al., Bull. Acad. Sci. USSR Div. Chem. 30, 2312 (1982).

*Primary Examiner*—Jacqueline V. Howard
*Attorney, Agent, or Firm*—Luther A. R. Hall

[57] ABSTRACT

Composition containing an organic polymer, with the exception of epoxy-based polymers, a lubricant, a metalworking fluid or a hydraulic fluid and, as stabilizer, at least one dioxaphosphorinane compound of the formulae

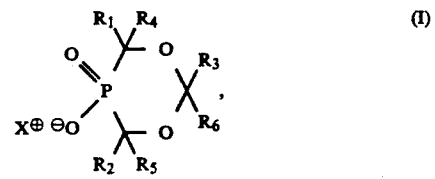

(I)

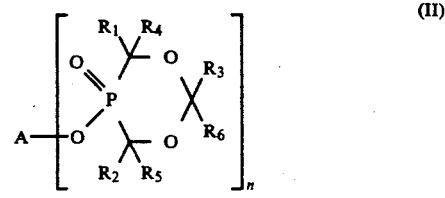

(II)

or/and

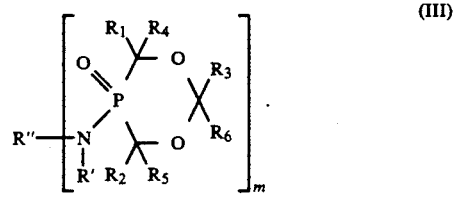

(III)

wherein $R_1$ to $R_6$, $R'$ and $R''$ are independently hydrogen, alkyl, alkenyl, cycloalkyl or aryl, $X^+$ is hydrogen, a metal cation or quaternary nitrogen atom, A is a n-valent hydrocarbyl moiety, n is 1 to 4, and m is 1 or 2.

These compositions are stabilized against thermal, oxidative and/or actinic degradation. The abovementioned compounds are also very suitable as wear-resistant agents and high-pressure additives in lubricants.

Some of the dioxaphosphorinane compounds are novel.

15 Claims, No Drawings

DIOXAPHOSPHORINANE COMPOUNDS AS STABILIZERS FOR ORGANIC MATERIALS

The present invention relates to compositions comprising an organic polymer, a lubricant, a metal-working fluid or a hydraulic fluid and at least one dioxaphosphorinane compound. The invention also relates to novel dioxaphosphorinane compounds.

Dioxaphosphorinanes and their preparation are described, for example in U.S. Pat. Nos. 2,984,551, 2,984,683, 3,005,020 and 3,328,319 and Izv. Akad. Nauk. SSSR, Ser. Khim 2803-6(12), 1981 and 2550-4(11), 1983. These publications also disclose various possible uses for compounds of this type. U.S. Pat. No. 3,005,020 discloses the use of dioxaphosphorinanes as complexing agents for the extraction of metals, in particular uranium, from ores. Their use as inhibitors of premature ignition in propellants is disclosed in U.S. Pat. No. 2,984,551 and as reaction accelerators for the curing of epoxy resins in U.S. Pat. No. 3,328,319.

It has now been found that dioxaphosphorinanes are very surprisingly suitable for stabilising polymers, lubricants, metal-working fluids and hydraulic fluids against oxidative, thermal and/or actinic degradation and as wear-resistant agents and high-pressure additives in lubricants.

Furthermore, novel dioxaphosphorinanes have been found which have the abovementioned property.

The present invention relates to compositions comprising an organic polymer, with the exception of polymers based on epoxy resin, a lubricant, a metal-working fluid or a hydraulic fluid and at least one dioxaphosphorinane compound of the formulae

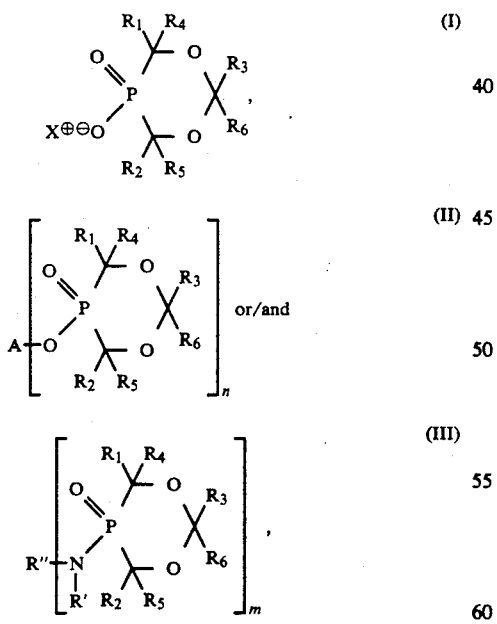

in which
$R_1$, $R_2$, $R_3$, $R_4$, $R_5$ and $R_6$, independently of one another, are hydrogen, $C_1$-$C_{18}$alkyl which is uninterrupted or interrupted by O, S or NH, $C_2$-$C_{12}$alkenyl, unsubstituted or $C_1$-$C_4$alkyl-substituted $C_5$-$C_{12}$cycloalkyl, cyclohexenyl, phenyl, which is unsubstituted or substituted with $C_1$-$C_{18}$alkyl, hydroxyl, $C_1$-$C_{18}$alkoxy, $C_2$-$C_{18}$alkoxycarbonyl or/and $C_1$-$C_{18}$alkylmercapto, or are a group

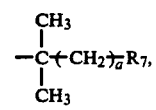

in which a is zero or one and $R_7$ is

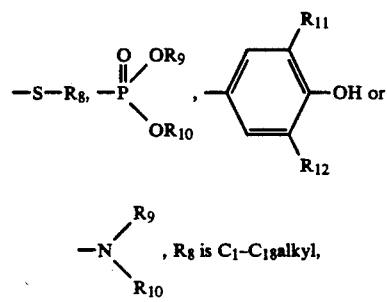

$C_2$-$C_{12}$alkenyl, phenyl, benzyl or —$CH_2$—$COOR_{13}$, $R_9$ and $R_{10}$, independently of one another, are hydrogen, $C_1$-$C_{18}$alkyl, $C_5$-$C_{12}$cycloalkyl or phenyl, $R_{11}$ and $R_{12}$, independently of one another, are hydrogen, $C_1$-$C_4$alkyl, cyclohexyl or phenyl, $R_{13}$ is hydrogen, $C_1$-$C_{18}$alkyl, $C_2$-$C_{12}$alkenyl, $C_5$-$C_{12}$cycloalkyl or benzyl, or $R_1$, $R_2$, $R_3$, $R_4$, $R_5$ and $R_6$, independently of one another, are a group —$COOR_{13}$,

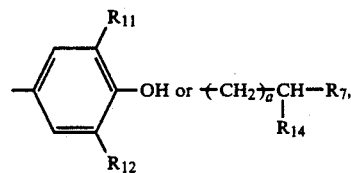

in which $R_7$, $R_{11}$, $R_{12}$, $R_{13}$ and a are as defined above and $R_{14}$ is hydrogen if a is zero and is hydrogen, methyl or phenyl if a is 1, $X^\oplus$ is $H^\oplus$ or a group of the formulae $(M^{r\oplus}/r)$ or $N^\oplus(R_{15})(R_{16})(R_{17})(R_{18})$, in which $M^{r\oplus}$ is an r-valent metal cation, R is the number 1, 2 or 3, $R_{15}$, $R_{16}$, $R_{17}$, $R_{18}$, independently of one another, are hydrogen, $C_1$-$C_{18}$alkyl, $C_5$-$C_{12}$cycloalkyl, unsubstituted or $C_1$-$C_{18}$alkyl-substituted phenyl or $R_{17}$ and $R_{18}$ together with the N atom form a pyrrolidine, imidazolidine, piperidine, piperazine or morpholine radical, or $R_{16}$, $R_{17}$ and $R_{18}$ together with the N atom form a pyridine, picoline, pyrazine, quinoline or isoquinoline radical, n is the number 1, 2, 3 or 4, if n is 1 A is $C_1$-$C_{30}$alkyl which is uninterrupted or interrupted by O, S or NH, $C_2$-$C_{12}$alkenyl, unsubstituted or $C_1$-$C_4$alkyl-substituted $C_5$-$C_{12}$cycloalkyl, benzyl, unsubstituted or $C_1$-$C_{18}$alkyl-substituted phenyl, a group

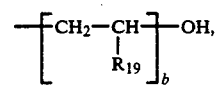

in which $R_{19}$ is hydrogen or methyl and b is a number from 1 to 10, or a radical

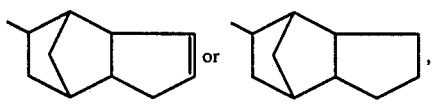

if n is 2, A is $C_2$–$C_{18}$alkylene or $C_2$–$C_{18}$alkylene which is interrupted by —O—, —NH— or —S—, if n is 3, A is a group —CH$_2$—CH—CH$_2$—, and if n is 4, A is a group C(CH$_2$)$_4$,
  | m is the number 1 or 2, in which, if m is 1,
R' and R", independently of one another, are hydrogen, $C_1$–$C_{18}$alkyl which is uninterrupted or interrupted by O, S or NH, $C_2$–$C_{12}$alkenyl, unsubstituted or $C_1$–$C_4$alkyl-substituted $C_5$–$C_{12}$cycloalkyl, unsubstituted or $C_1$–$C_{18}$alkyl-substituted phenyl, benzyl or a group

—CH$_2$—CH—Y—R$_{20}$,
     |
    R$_{19}$ in which Y is —O— or —NH—, R$_{19}$ has the abovementioned meaning and R$_{20}$ is hydrogen, —CO–($C_1$–$C_{18}$alkyl) or —CO–($C_2$–$C_{12}$alkenyl), or R' is hydrogen and R" is $C_1$–$C_{12}$alkoxy, a group

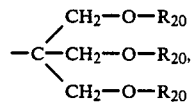

in which R$_{20}$ is as defined above, or a group

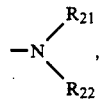

in which R$_{21}$ and R$_{22}$, independently of one another, are hydrogen, $C_1$–$C_{18}$alkyl, $C_2$–$C_{12}$alkenyl, unsubstituted or $C_1$–$C_{18}$alkyl-substituted phenyl, —CO–($C_1$–$C_{18}$alkyl) or —CO–($C_2$–$C_{12}$alkenyl), benzoyl or together a group =CH—R$_{23}$, in which R$_{23}$ is hydrogen, $C_1$–$C_{18}$alkyl, $C_2$–$C_{12}$alkenyl, $C_5$–$C_{12}$cycloalkyl or phenyl, or
R' and R" together with the nitrogen atom to which they are bound form a pyrrolidine, imidazolidine, piperidine, piperazine or morpholine radical, and if m is 2,
R' is hydrogen and R" is $C_2$–$C_{18}$alkylene.

$C_1$–$C_{18}$Alkyl substituents are branched or unbranched radicals. Examples of these are methyl, ethyl, propyl, isopropyl, n-butyl, isobutyl, t-butyl, pentyl, isopentyl, hexyl, heptyl, 3-heptyl, octyl, 2-ethylhexyl, nonyl, decyl, undecyl, dodecyl, tridecyl, tetradecyl, pentadecyl, hexadecyl, heptadecyl, octadecyl, 2-ethylbutyl, 1-methylpentyl, 1,3-dimethylbutyl, 1,1,3,3-tetramethylbutyl, 1-methylhexyl, isoheptyl, 1-methylheptyl, 1,1,3-trimethylhexyl or 1-methylundecyl. The radical A as $C_1$–$C_{30}$alkyl is additionally also, for example, eicosyl, heneicosyl, tricosyl, tetracosyl, pentacosyl or triacontyl. $C_1$–$C_4$Alkyl radicals are methyl, ethyl, propyl, isopropyl, n-butyl, isobutyl or t-butyl.

$C_2$–$C_{12}$Alkenyl substituents can be branched or unbranched alkenyl, for example vinyl, allyl, 2-methylallyl, hexenyl, decenyl and dodecenyl.

Any substituent which can be $C_5$–$C_{12}$cycloalkyl, is, for example, cyclopentyl, cyclohexyl, cycloheptyl, cyclooctyl or cyclododecyl. Cyclopentyl and in particular cyclohexyl are preferred.

Examples of any $C_1$–$C_{18}$alkoxy groups are derived from the radicals listed above for $C_1$–$C_{18}$alkyl groups and can be defined formally by adding the suffix -oxy. The same is true of any $C_1$–$C_{18}$alkylmercapto groups but with the suffix -mercapto.

$X^\oplus$ is preferably $H^\oplus$ or in particular a group of formula ($M^{r\oplus}$/r).

In a group of the formula ($M^{r\oplus}$/r) as $X^\oplus$, $M^{r\oplus}$ is, for example, an alkali metal cation, alkaline earth metal cation, aluminium cation or transition metal cation, for example $Na^\oplus$, $K^\oplus$, $Mg^{2\oplus}$, $Ca^{2\oplus}$, $Sr^{2\oplus}$, $Ba^{2\oplus}$, $Zn^{2\oplus}$, $Mn^{2\oplus}$, $Cu^{2\oplus}$, $Ni^{2\oplus}$, $Cd^{2\oplus}$, $Co^{3\oplus}$, $Al^{3\oplus}$ und $Cr^{3\oplus}$, but in particular a mono- or divalent metal cation (r=1 or 2) and preferably $Na^\oplus$, $K^\oplus$, $Ca^{2\oplus}$, $Mg^{2\oplus}$, $Zn^{2\oplus}$, $Cu^{2\oplus}$ or $Ni^{2\oplus}$.

R$_{15}$, R$_{16}$, R$_{17}$ and R$_{18}$ as $C_5$–$C_6$cycloalkyl are, for example, cyclopentyl or in particular cyclohexyl.

R$_{15}$, R$_{16}$, R$_{17}$ and R$_{18}$ as $C_1$–$C_{18}$alkyl-substituted phenyl are preferably $C_{12}$–$C_{18}$alkyl-substituted phenyl.

Examples of suitable $N^\oplus(R_{15})(R_{16})(R_{17})(R_{18})$ are: $N^\oplus H_4$, $N^\oplus H_3 CH_3$, $N^\oplus H_2(CH_3)_2$, $N^\oplus H_3 C_2 H_5$, $N^\oplus H_2(C_2H_5)_2$, $N^\oplus H_3$-iso-$C_3H_7$, $N^\oplus H_3$-n-octadecyl, $N^\oplus H_3$-cyclohexyl, $N^\oplus H_2$-(cyclohexyl)$_2$, $N^\oplus H_2(CH_3)(C_6H_5)$, $N^\oplus H_3 C_6 H_5$, $N^\oplus H_3$-p-octadecylphenyl and $N^\oplus(CH_3)_4$.

Compositions comprising compounds of the formulae I, II or III, in which R$_1$, R$_2$ and R$_3$ are identical and are as defined above and R$_4$, R$_5$ and R$_6$ are hydrogen, are of particular interest.

Compositions according to the invention comprising compounds of the formulae I, II or III, in which R$_1$, R$_2$ and R$_3$ are identical and are $C_1$–$C_{18}$alkyl, cyclohexyl, cyclohexenyl or a group

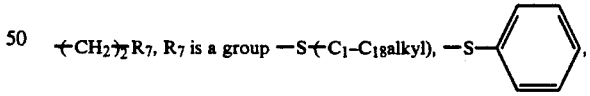

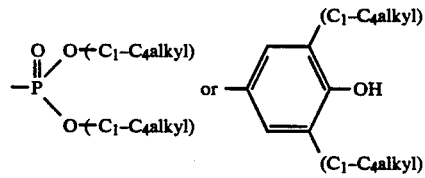

and R$_4$, R$_5$ and R$_6$ are hydrogen, are of very particular interest.

Preference is given to compositions according to the invention comprising compounds of the formulae I, II and III, in which R$_1$, R$_2$, R$_3$, R$_4$, R$_5$ and R$_6$ have the abovementioned first and in particular second preferred meaning and $X^\oplus$ is $H^\oplus$ or a group of the formulae ($M^{r\oplus}$/r) or $N^\oplus(R_{15})(R_{16})(R_{17})(R_{18})$, in which $M^{r\oplus}$ is a mono- or divalent metal cation and $R_{15}$, $R_{16}$, $R_{17}$, $R_{18}$, independently of one another, are hydrogen, $C_1$–$C_{12}$alkyl or cyclohexyl, n is the number 1 or 2, if n is 1, A is $C_1$–$C_{18}$alkyl, cyclohexyl, unsubstituted or $C_1$–$C_4$alkyl-substituted phenyl or benzyl, if n is 2, A is $C_2$–$C_{12}$alkylene or $C_2$–$C_{12}$alkylene which is interrupted by —O— or —S—, m is the number 1 or 2, in which, if m is 1, R' and R", independently of one another, is hydrogen, $C_1$–$C_{18}$alkyl, cyclohexyl, phenyl, benzyl or hydroxy-$C_1$–$C_4$alkyl, or R' is hydrogen and R" is amino, $C_1$–$C_6$alkylamino, $C_2$–$C_{12}$dialkylamino, $C_1$–$C_6$alkoxy or a group

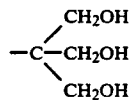

or R' and R" together with the N atom form a piperidine, piperazine or morpholine radical, or, if m is 2, R' is hydrogen and R" is $C_2$–$C_{12}$alkylene, in which $X^\oplus$ is preferably $H^\oplus$, $Na^\oplus$, $K^\oplus$, $Ca^{2\oplus}/2$, $Mg^{2\oplus}/2$, $Zn^{2\oplus}/2$, $Cu^{2\oplus}/2$ or $Ni^{2\oplus}/2$, A is $C_1$–$C_{18}$alkyl, phenyl, benzyl, $C_2$–$C_{12}$alkylene or $C_2$–$C_{12}$alkylene which is interrupted by —O— or —S—, R' and R", independently of one another, are hydrogen, $C_1$–$C_{12}$alkyl, phenyl, benzyl or hydroxy-$C_2$–$C_4$alkyl or R' is hydrogen and R" is $C_1$–$C_4$alkoxy, amino or $C_2$–$C_{18}$alkylene, or R' and R" together with the N atom form a piperidine, piperazine or morpholine radical.

Particular mention may be made of compositions according to the invention comprising compounds of the formulae I, II or III in which $X^\oplus$ is $H^\oplus$, $Na^\oplus$, $K^\oplus$, $Ca^{2\oplus}/2$, $Mg^{2\oplus}/2$, $Zn^{2\oplus}/2$, $Cu^{2\oplus}/2$, $Ni^{2\oplus}/2$ or $\oplus N(R_{15})(R_{16})(R_{17})(R_{18})$ and $R_{15}$, $R_{16}$, $R_{17}$ and $R_{18}$, independently of one another, are hydrogen or $C_1$–$C_6$alkyl, n is the number 1 or 2, if n is 1 A is $C_1$–$C_{12}$alkyl, and if n is 2, A is $C_2$–$C_{12}$alkylene or $C_2$–$C_{12}$alkylene which is interrupted by —O—, m is the number 1 or 2, in which, if m is 1, R' and R", independently of one another, are hydrogen, $C_1$–$C_6$alkyl, hydroxy-$C_2$–$C_4$alkyl, or R' is hydrogen and R" is amino or $C_1$–$C_4$alkoxy, or R' and R" together with the N atom form a piperidine, piperazine or morpholine radical, if m is 2, R' is hydrogen and R" is $C_2$–$C_{18}$alkylene, $R_1$, $R_2$ and $R_3$ are identical or $C_1$–$C_{12}$alkyl, cyclohexenyl or a group of the formula —$(CH_2)_2$—$R_7$, in which $R_7$ is —S—$C_1$–$C_{14}$alkyl,

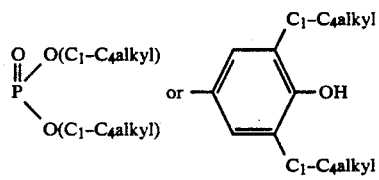

and $R_4$, $R_5$ and $R_6$ are hydrogen.

The dioxaphosphorinanes of the formulae I, II and/or III are advantageously present in the compositions according to the invention in amounts of 0.001 to 10, for example 0.05 to 5, preferably 0.01 to 5, but in particular 0.1 to 2, % by weight, relative to the materials to be stabilised (for example polymers, lubricants, and the like). One or more of these compounds can be used, and the percentages by weight are based on the entire amount of these compounds.

Examples of polymers which can be stabilised according to the invention by means of the compounds of the formulae I, II and/or III are:

1. Polymers of mono- and diolefins, for example polypropylene, polyisobutylene, polybut-1-ene, polymethylpent-1-ene, polyisoprene or polybutadiene, as well as polymers of cycloolefins, for example of cyclopentene or norbornene; as well as polyethylene (which if desired can be crosslinked), for example high-density polyethylene (HDPE), low-density polyethylene (LDPE) and linear low-density polyethylene (LLDPE).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of mono- and diolefins with each other or with other vinyl monomers, for example ethylene/propylene copolymers, linear low-density polyethylene (LLDPE) and its mixtures with low-density polyethylene (LDPE), propylene/1-butene copolymers, propylene/isobutylene copolymers, ethylene/1-butene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and their salts (ionomers) and terpolymers of ethylene with propylene and a diene, such as hexadiene, dicyclopentadiene or ethylidenenorbornene; as well as mixtures of such copolymers with each other and with polymers mentioned under 1), for example polypropylene and ethylene/propylene copolymers, LDPE and ethylene/vinyl acetate copolymers, LDPE and ethylene/acrylic acid copolymers, LLDPE and ethylene/vinyl acetate copolymers and LLDPE and ethylene/acrylic acid copolymers.

3a. Hydrocarbon resins (for example $C_5$–$C_9$), including hydrogenated modifications thereof (for example tackifier resins).

4. Polystyrene, poly(p-methylstyrene), poly(α-methylstyrene).

5. Copolymers of styrene or α-methylstyrene with dienes or acrylic derivatives, for example, styrene/butadiene, styrene/acrylonitrile, styrene/alkyl methacrylate, styrene/butadiene/alkyl acrylate, styrene/maleic anhydride, styrene/acrylonitrile/methyl acrylate; mixtures of high impact strength composed of styrene copolymers and another polymer, for example from a polyacrylate, a diene polymer or an ethylene/propylene/diene terpolymer; and block copolymers of styrene, for example styrene/butadiene/styrene, styrene/isoprene/styrene, styrene/ethylene/butylene/styrene or styrene/ethylene/propylene/styrene.

6. Graft copolymers of styrene or α-methylstyrene, for example styrene on polybutadiene, styrene on copolymers of polybutadiene/styrene or polybutadiene/acrylonitrile, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates or alkyl methacrylates on polybutadiene, styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 5), for example those known as so-called ABS, MBS, ASA and AES polymers.

7. Halogen-containing polymers, for example polychloroprene, chlorinated rubber, chlorinated or sulfochlorinated polyethylene, copolymers of ethylene and chlorinated ethylene, epichlorohydrin homo- and copolymers, in particular polymers from halogen-containing vinyl compounds, for example polyvinyl chloride, polyvinylidene chloride, polyvinyl fluoride, polyvinylidene fluoride; as well as copolymers thereof, such as vinyl chloride/vinylidene chloride, vinyl chloride/vinyl acetate or vinylidene chloride/vinyl acetate.

8. Polymers which are derived from $\alpha,\beta$-unsaturated acids and derivatives thereof, such as polyacrylates and polymethacrylates, polyacrylamides and polyacrylonitriles.

9. Copolymers of the monomers mentioned under 8) with each other or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinyl butyral, polyallyl phthalate or polyallylmelamine; as well as their copolymers with olefins mentioned in 1).

11. Homo- and copolymers of cyclic ethers, such as polyalkylene glycols, polyethylene oxide or polypropylene oxide.

12. Polyacetals, such as polyoxymethylene and those polyoxymethylenes which contain comonomers such as ethylene oxide; polyacetals modified with thermoplastic polyurethanes, acrylates or MBS.

13. Polyphenylene oxides and sulfides, and mixtures thereof with styrene polymers or polyamides.

14. Polyurethanes which are derived from polyethers, polyesters and polybutadienes with terminal hydroxyl groups on the one hand and aliphatic or aromatic polyisocyanates on the other hand, as well as precursors thereof.

15. Polyamides and copolyamides which are derived from diamines and dicarboxylic acids and/or from aminocarboxylic acids or the corresponding lactams, such as nylon 4, nylon 6, nylon 6/6, 6/10, 6/9, 6/12 and 4/6, nylon 11, nylon 12, aromatic polyamides obtained starting from m-xylene, diamine and adipic acid; polyamides prepared from hexamethylenediamine and isophthalic and/or terephthalic acid and if desired an elastomer as modifier, for example poly-2,4,4-trimethylhexamethyleneterephthalamide or poly-m-phenyleneisophthalamide. Block copolymers of the aforementioned polyamides with polyolefins, olefin copolymers, ionomers or chemically bonded or grafted elastomers; or with polyethers, for example with polyethylene glycol, polypropylene glycol or polytetramethylene glycol. In addition, polyamides or copolyamides modified with EPDM or ABS; as well as polyamides condensed during processing ("RIM-polyamide systems").

16. Polyureas, polyimides, polyamide-imides and polybenzimidazoles.

17. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate, polyhydroxybenzoates, as well as block polyether esters derived from polyethers having hydroxyl end groups; in addition polyesters modified with polycarbonates or MBS.

18. Polycarbonates and polyester carbonates.

19. Polysulfones, polyether sulfones and polyether ketones.

20. Crosslinked polymers which are derived from aldehydes on the one hand and phenols, urea or melamine on the other hand, such as phenol/formaldehyde, urea/formaldehyde and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Crosslinkable acrylic resins, derived from substituted acrylic esters, for example from urethane acrylates or polyester acrylates.

24. Alkyd resins, polyester resins or acrylate resins which are crosslinked with melamine resins, urea resins or polyisocyanates.

25. Natural polymers, such as cellulose, natural rubber, gelatin, and their polymer-homologous chemically modified derivatives, such as cellulose acetates, propionates and butyrates, or cellulose ethers, such as methylcellulose; and rosin resins and their derivatives.

26. Mixtures (polyblends) of the polymers mentioned above, for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6/6 and copolymers, PA/HDPE, PA/PP, PA/PPO.

Compositions which contain a polymer, in particular a thermoplastic or an elastomer, are particularly preferred. Compositions containing a polyolefin as polymer should be mentioned in particular.

Compositions are also preferred which comprise a lubricant, a metal-working processing fluid or a hydraulic fluid, in particular a lubricant.

Suitable lubricants are based, for example, on mineral or synthetic oils or mixtures thereof. The lubricants are familiar to the person skilled in the art and are described in the relevant specialist literature, for example in Dieter Klamann, "Schmierstoffe und verwandte Produkte" [Lubricants and Related Products] (Verlag Chemie, Weinheim, 1982), in Schewe-Kobek, "Das Schmiermittel-Taschenbuch" [The Lubricant Handbook] (Dr. Alfred Hüthig-Verlag, Heidelberg, 1974) and in "Ullmanns Enzyklopädie der technischen Chemie" [Ullmann's Encyclopaedia of Industrial Chemistry], vol. 13, pages 85–94 (Verlag Chemie, Weinheim, 1977).

The lubricants are in particular oils and fats, for example based on a mineral oil. Oils are preferred.

A further group of lubricants which can be used are vegetable or animal oils, fats, tallows and waxes or mixtures thereof with each other or mixtures with the mineral or synthetic oils mentioned. Vegetable and animal oils, fats, tallows and waxes are, for example, palm kernel oil, palm oil, olive oil, colza oil, rapeseed oil, linseed oil, groundnut oil, soya bean oil, cotton oil, sunflower oil, pumpkin seed oil, coconut oil, corn oil, castor oil, walnut oil and mixtures thereof, fish oils, tallows from slaughtered animals such as bovine tallow, neatsfoot oil and bone oil and their modified, epoxidised and sulfoxidised forms, for example epoxidised soya bean oil.

The mineral oils are based in particular on hydrocarbon compounds.

Examples of synthetic lubricants include lubricants based on aliphatic or aromatic carboxylic esters, polymeric esters, polyalkylene oxides, phosphoric acid esters, poly-$\alpha$-olefins or silicones, on a diester of a dibasic acid with a monohydric alcohol, for example dioctyl sebacate or dinonyl adipate, on a triester or trimethylolpropane with a monobasic acid or with a mixture of such acids, for example trimethylolpropane tripelargonate, trimethylolpropane tricaprylate or mixtures thereof, on a tetraester of pentaerythritol with a monobasic acid or with a mixture of such acids, such as pentaerythritol tetracaprylate, or on a complex ester of monobasic and dibasic acids with polyhydric alcohols, for example a complex ester of trimethylolpropane with caprylic and sebacic acid or on a mixture thereof. Particularly suitable in addition to mineral oils are, for example, poly-$\alpha$-olefins, lubricants based on esters, phosphates, glycols, polyglycols and polyalkylene glycols, and mixtures thereof with water.

Metal-working fluids and hydraulic fluids can be prepared based on the same substances as described above for the lubricants. Frequently, these are also emulsions of such substances in water or other fluids.

Incorporation into the above-mentioned organic materials can be carried out, for example, by mixing in the compounds of the formulae I, II and/or III and, if desired, other additives by the methods customary in industry. In the case of polymers, in particular synthetic polymers, incorporation can be carried out before or during moulding, or by applying the dissolved or dispersed compounds to the polymer, if appropriate with subsequent evaporation of the solvent. In the case of elastomers, these can also be stabilised as latices. A further possibility of incorporation of the compounds of the formulae I, II and or III in polymers comprises their addition before, during, or immediately after polymerisation of the corresponding monomers or before crosslinking. They can be added as such but also in encapsulated form (for example in waxes, oils or polymers). In the case of addition before or during polymerisation, the compounds of the formulae I, II and/or III can also act as regulators for the chain length of the polymers (chain terminators).

The compounds of the formulae I, II and/or III or mixtures thereof can also be added to the plastics to be stabilised in the form of a masterbatch which contains these compounds, for example, in a concentration of 2.5 to 25% by weight.

The incorporation of the compounds of the formulae I, II and/or III can expediently be carried out by the following methods:

as an emulsion or dispersion (for example addition to latices or emulsion polymers)

as a dry mixture during mixing of additional components or polymer mixtures by direct addition to the processing apparatus (for example extruders, internal mixers etc.)

as a solution or melt.

Polymer compositions according to the invention can be used in various forms or processed to give various products, for example as (to give) sheets, fibres, tapes, moulded articles, profiles or as binders for paints, adhesives or cements.

Lubricant compositions according to the invention are used, for example, in internal combustion motors, for example in motor vehicles.

In addition to the compounds or mixtures according to the invention, the compositions according to the invention can contain still other customary additives, in particular if they contain polymers, preferably synthetic polymers. Examples of such additives are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, 2,6-dinonyl-4-methylphenol.

1.2. Alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol.

1.3. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol).

1.4. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-($\alpha$-methylbenzyl)-4-nonylphenol], 2,2'-methylenebis[6-($\alpha,\alpha$-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)-dicyclopentadiene, bis[2-(3'-tert-butyl-2'-hydroxy-5'-methylbenzyl)-6-tert-butyl-4-methylphenyl]terephthalate.

1.5. Benzyl compounds, for example 1,3,5-tris(3,5-di-tert-butyl-4-hydroxybenzyl)-2,4,6-trimethylbenzene, bis(3,5-di-tert-butyl-4-hydroxybenzyl) sulfide, isooctyl 3,5-di-tert-butyl-4-hydroxybenzylmercaptoacetate, bis(4-tert-butyl-3-hydroxy-2,6-dimethylbenzyl) dithioterephthalate, 1,3,5-tris(3,5-di-tert-butyl-4-hydroxybenzyl) isocyanurate, 1,3,5-tris(4-tert-butyl-3-hydroxy-2,6-dimethylbenzyl) isocyanurate, dioctadecyl 3,5-di-tert-butyl-4-hydroxybenzylphosphonate, calcium salt of monoethyl 3,5-di-tert-butyl-4-hydroxybenzylphosphonate, 1,3,5-tris(3,5-dicyclohexyl-4-hydroxybenzyl) isocyanurate.

1.6. Acylaminophenols, for example 4-hydroxylauranilide, 4-hydroxystearanilide, 2,4-bis(octylmercapto)-6-(3,5-di-tert-butyl-4-hydroxyanilino)-s-triazine, octyl N-(3,5-di-tert-butyl-4-hydroxyphenyl) carbamate.

1.7. Esters of β-(3,5-di-tert-butyl-4-hydroxyphenyl)propionic acid with mono- or polyhydric alcohols, for example with methanol, octadecanol, 1,6-hexanediol, neopentyl glycol, thiodiethylene glycol, diethylene glycol, triethylene glycol, pentaerythritol, tris(hydroxyethyl) isocyanurate, N,N'-bis(hydroxyethyl)oxalamide.

1.8. Esters of β-(5-tert-butyl-4-hydroxy-3-methylphenyl)propionic acid with mono- or polyhydric alcohols, for example with methanol, octadecanol, 1,6-hexanediol, neopentyl glycol, thiodiethylene glycol, diethylene glycol, triethylene glycol, pentaerythritol, tris(hydroxyethyl) isocyanurate, N,N'-bis(hydroxyethyl)oxalamide.

1.9. Esters of β-(3,5-dicyclohexyl-4-hydroxyphenyl)propionic acid with mono- or polyhydric alcohols, for example with methanol, octadecanol, 1,6-hexanediol, neopentyl glycol, thiodiethylene glycol, diethylene glycol, triethylene glycol, pentaerythritol, tris(hydroxyethyl) isocyanurate, N,N'-bis(hydroxyethyl)oxalamide.

1.10. Amides of β-(3,5-di-tert-butyl-4-hydroxyphenyl)propionic acid, for example N,N'-bis(3,5-di-tert-butyl-4-hydroxyphenylpropionyl)hexamethylenediamine, N,N'-bis(3,5-di-tert-butyl-4-hydroxyphenylpropionyl)trimethylenediamine, N,N'-bis(3,5-di-tert-butyl-4-hydroxyphenylpropionyl)hydrazine.

2. UV absorbers and light stabilisers 2.1. 2-(2'-Hydroxyphenyl)benzotriazoles, for example the 5'-methyl, 3',5'-di-tert-butyl, 5'-tert-butyl, 5'-(1,1,3,3-tetramethylbutyl), 5-chloro-3',5'-di-tert-butyl, 5-chloro-3'-tert-butyl-5'-methyl, 3'-sec-butyl-5'-tert-butyl, 4'-octoxy, 3',5'-di-tert-amyl and 3',5'-bis-(α,α-dimethylbenzyl) derivative.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

2.3. Esters of unsubstituted or substituted benzoic acids, for example 4-tert-butylphenyl salicylate, phenyl salicylate, octylphenyl salicylate, dibenzoylresorcinol, bis(4-tert-butylbenzoyl)resorcinol, benzoylresorcinol, 2,4-di-tert-butylphenyl 3,5-di-tert-butyl-4-hydroxybenzoate and hexadecyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of monoalkyl 4-hydroxy-3,5-di-tert-butylbenzylphosphonates, such as those of the methyl or ethyl ester, nickel complexes of ketoximes, such as 2-hydroxy-4-methylphenyl undecyl ketoxime, nickel complexes of 1-phenyl-4-lauroyl-5-hydroxypyrazole, with or without additional ligands.

2.6. Sterically hindered amines, for example bis(2,2,6,6-tetramethylpiperidyl) sebacate, bis(1,2,2,6,6-pentamethylpiperidyl) sebacate, bis(1,2,2,6,6-pentamethylpiperidyl) n-butyl-3,5-di-tert-butyl-4-hydroxybenzylmalonate, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl) nitrilotriacetate, tetrakis(2,2,6,6-tetramethyl-4-piperidyl) 1,2,3,4-butanetetracarboxylate, 1,1'-(1,2-ethanediyl)bis(3,3,5,5-tetramethylpiperazinone).

2.7. Oxalamides, for example, 4,4'-dioctyloxyoxanilide, 2,2'-dioctyloxy-5,5'-di-tert-butyloxanilide, 2,2'-didodecyloxy-5,5'-di-tert-butyloxanilide, 2-ethoxy-2'-ethyloxanilide, N,N'-bis(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of o- and p-methoxy-disubstituted oxanilides, and o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine.

3. Metal deactivators, for example N,N'-diphenyloxalamide, N-salicylal-N'-salicyloylhydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalic dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, tristearyl sorbitol triphosphite, tetrakis(2,4-di-tert-butylphenyl) 4,4'-biphenylenediphosphonite.

5. Compounds which destroy peroxides, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

6. Polyamide stabilisers, for example copper salts in combination with iodides and/or phosphorus compounds and salts of divalent manganese.

7. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium stearate, sodium ricinoleate and potassium palmitate, antimony pyrocatecholate or zinc pyrocatecholate.

8. Nucleating agents, for example 4-tert-butylbenzoic acid, adipic acid, diphenylacetic acid.
9. Fillers and reinforcing agents, for example calcium carbonate, silicates, glass fibres, asbestos, talc, kaolin, mica, barium sulfate, metal oxides and hydroxides, carbon black, graphite.
10. Other additives, for example plasticisers, lubricants, emulsifiers, pigments, fluorescent whitening agents, flameproofing agents, antistatic agents and blowing agents.

The compositions according to the invention based on lubricants and hydraulic fluids or metal-working fluids can also contain other additives which are added to improve certain use properties, for example other antioxidants, metal deactivators, rust inhibitors, viscosity index improvers, pour point reducers, dispersants/surfactants and abrasion resistance additives.

Examples of antioxidants can be seen from the listing reproduced above under the title "1. Antioxidants", in particular items 1.1 to 1.10. Examples of other additional additives are the following:

Examples of amine antioxidants

N,N'-di-isopropyl-p-phenylenediamine, N,N'-di-sec-butyl-p-phenylenediamine, N,N'-bis(1,4-dimethyl-pentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2)-p-phenylenediamine, N-isopropyl-N'-phenyl-p-phenylenediamine, N-(1,3-dimethyl-butyl)-N'-phenyl-p-phenylenediamine, N-(1-methyl-heptyl)-N'-phenyl-p-phenylenediamine, N-cyclohexyl-N'-phenyl-p-phenylenediamine, 4-(p-toluene-sulfonamido)-diphenylamine, N,N'-dimethyl-N,N'-di-sec-butyl-p-phenylenediamine, diphenylamine, N-allyldiphenylamine, 4-isopropoxy-diphenylamine, N-phenyl-1-naphthylamine, N-phenyl-2-naphthylamine, octylated diphenylamine, such as p,p'-di-tert-octyldiphenylamine, 4-n-butylaminophenol, 4-butyrylamino-phenol, 4-nonanoylamino-phenol, 4-dodecanoylamino-phenol, 4-octadecanoylamino-phenol, di-(4-methoxyphenyl)-amine, 2,6-di-tert-butyl-4-dimethylamino-methyl-phenol, 2,4'-diamino-diphenylmethane, 4,4'-diamino-diphenylmethane, N,N,N',N'-tetramethyl-4,4'-diamino-diphenylmethane, 1,2-di-[(2-methyl-phenyl)-amino]-ethane, 1,2-di-(phenylamino)-propane, (o-tolyl)-biguanide, di-[4-(1',3'-dimethyl-butyl)-phenyl]amine, tert-octylated N-phenyl-1-naphthylamine, mixture of mono- and dialkylated tert-butyl/tert-octyldiphenylamines, 2,3-dihydro-3,3-dimethyl-4H-1,4-benzothiazine, phenothiazine, N-allylphenothiazine.

Examples of other antioxidants: aliphatic or aromatic phosphites, esters of thiodipropionic acid or thiodiacetic acid, or salts of dithiocarbamic or dithiophosphoric acid.

Examples of metal deactivators, for example for copper, are: triazoles, benzotriazoles and derivatives thereof, tolutriazoles and derivatives thereof, 2-mercaptobenzothiazole, 2-mercaptobenzotriazole, 2,5-dimercaptobenzothiazole, 2,5-dimercaptobenzothiadiazole, 5,5'-methylenebisbenzotriazole, 4,5,6,7-tetrahydrobenzotriazole, salicylidenepropylenediamine, salicylaminoguanidine and salts thereof.

Examples of rust inhibitors are:

a) Organic acids, their esters, metal salts and anhydrides, for example: N-oleoylsarcosine, sorbitan monooleate, lead naphthenate, alkenylsuccinic anhydride, for example dodecenylsuccinic anhydride, alkenylsuccinic acid partial esters and partial amines, 4-nonylphenoxyacetic acid.

b) Nitrogen-containing compounds, for example:
I. Primary, secondary or tertiary aliphatic or cycloaliphatic amines and amine salts of organic and inorganic acids, for example oil-soluble alkylammonium carboxylates.
II. Heterocyclic compounds, for example: substituted imidazolines and oxazolines.

c) Phosphorus-containing compounds, for example: amine salts of phosphoric acid partial esters or phosphonic acid partial esters, zinc dialkyldithiophosphates.

d) Sulfur-containing compounds, for example: barium dinonylnaphthalenesulfonates, calcium petroleumsulfonates.

Examples of viscosity index improvers are: polyacrylates, polymethacrylates, vinylpyrrolidone/methacrylate copolymers, polyvinylpyrrolidones, polybutenes, olefin copolymers, styrene/acrylate copolymers, polyethers.

Examples of pour point reducers are: polymethacrylate, alkylated naphthalene derivatives.

Examples of dispersants/surfactants are: polybutenylsuccinamides or -imides, polybutenylphosphonic acid derivatives, basic magnesium sulfonates and phenolates, calcium sulfonates and phenolates, and barium sulfonates and phenolates.

Examples of abrasion-resistant additives are: sulfur-and/or phosphorus-and/or halogen-containing compounds, such as sulfurised vegetable oils, zinc dialkyldithiophosphates, tritolyl phosphate, chlorinated paraffins, alkyl and aryl di- and trisulfides, triphenyl phosphorothionates, diethanolaminomethyltolyltriazole, di(2-ethylhexyl)aminomethyltolyltriazole.

The dioxaphosphorinane compounds of the formulae I, II and III, in which at least one of $R_1$, $R_2$, $R_3$, $R_4$, $R_5$ and $R_6$ is a group

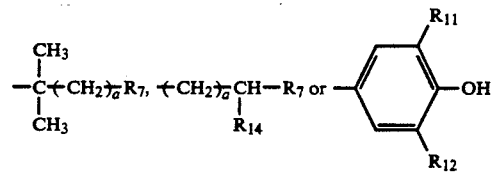

as defined above, are novel and also provided by the present invention.

Accordingly, the invention also relates to compounds of the formulae I, II and III

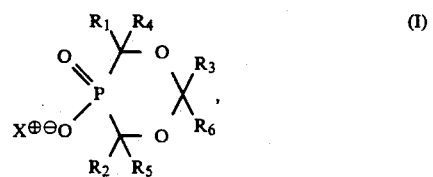

(I)

-continued $$A\left[O-P(=O)\begin{pmatrix}R_1\\R_2\end{pmatrix}\begin{pmatrix}R_4\\R_5\end{pmatrix}\begin{pmatrix}O\\O\end{pmatrix}\begin{pmatrix}R_3\\R_6\end{pmatrix}\right]_n \quad (II)$$

$$R''\underset{R'}{N}-P(=O)\begin{pmatrix}R_1\\R_2\end{pmatrix}\begin{pmatrix}R_4\\R_5\end{pmatrix}\begin{pmatrix}O\\O\end{pmatrix}\begin{pmatrix}R_3\\R_6\end{pmatrix}_m \quad (III)$$

in which $R_1$, $R_2$, $R_3$, $R_4$, $R_5$ and $R_6$, independently of one another, are hydrogen, $C_1$–$C_{18}$alkyl which is uninterrupted or interrupted by O, S or NH, $C_2$–$C_{12}$alkenyl, unsubstituted or $C_1$–$C_4$alkyl-substituted $C_5$–$C_{12}$cycloalkyl, cyclohexenyl, phenyl, which is unsubstituted or substituted with $C_1$–$C_{18}$alkyl, hydroxyl, $C_1$–$C_{18}$alkoxy, $C_2$–$C_{18}$alkoxycarbonyl or/and $C_1$–$C_{18}$alkylmercapto, or are a group $$-\underset{CH_3}{\overset{CH_3}{C}}(CH_2)_{\overline{a}}R_7,$$

in which a is zero or one and $R_7$ is $$-S-R_8, \quad -P(=O)\begin{pmatrix}OR_9\\OR_{10}\end{pmatrix},$$

[phenyl group with $R_{11}$, $R_{12}$, OH] or $$-N\begin{pmatrix}R_9\\R_{10}\end{pmatrix}, \quad R_8 \text{ is } C_1-C_{18}\text{alkyl},$$

$C_2$–$C_{12}$alkenyl, phenyl, benzyl or —CH$_2$—COOR$_{13}$, $R_9$ and $R_{10}$, independently of one another, are hydrogen, $C_1$–$C_{18}$alkyl, $C_5$–$C_{12}$cycloalkyl or phenyl, $R_{11}$ and $R_{12}$, independently of one another, are hydrogen, $C_1$–$C_4$alkyl, cyclohexyl or phenyl, $R_{13}$ is hydrogen, $C_1$–$C_{18}$alkyl, $C_2$–$C_{12}$alkenyl, $C_5$–$C_{12}$cycloalkyl or benzyl, or $R_1$, $R_2$, $R_3$, $R_4$, $R_5$ and $R_6$, independently of one another, are a group —COOR$_{13}$,

[phenyl group with $R_{11}$, $R_{12}$]—OH or $-(CH_2)_{\overline{a}}\underset{R_{14}}{CH}-R_7$, in which $R_7$, $R_{11}$, $R_{12}$, $R_{13}$ and a have the abovementioned meaning and $R_{14}$ is hydrogen if a is zero and is hydrogen, methyl or phenyl if a is 1, on the condition that at least one of $R_1$, $R_2$, $R_3$, $R_4$, $R_5$ and $R_6$ must be a group $$-\underset{CH_3}{\overset{CH_3}{C}}(CH_2)_{\overline{a}}R_7, \quad -(CH_2)_{\overline{a}}\underset{R_{14}}{CH}-R_7 \text{ or } [\text{phenyl group with } R_{11}, R_{12}, OH]$$

as defined above, $X^\oplus$ is $H^\oplus$ or a group of the formulae ($M^{r\oplus}/r$) or $N^\oplus(R_{15})(R_{16})(R_{17})(R_{18})$, in which $M^{r\oplus}$ is an r-valent metal cation, r is the number 1, 2 or 3, $R_{15}$, $R_{16}$, $R_{17}$, $R_{18}$, independently of one another, are hydrogen, $C_1$–$C_{18}$alkyl, $C_5$–$C_{12}$cycloalkyl, unsubstituted or $C_1$–$C_{18}$alkyl-substituted phenyl or $R_{17}$ and $R_{18}$ together with the N atom form a pyrrolidine, imidazolidine, piperidine, piperazine or morpholine radical, or $R_{16}$, $R_{17}$ and $R_{18}$ together with the N atom form a pyridine, picoline, pyrazine, quinoline or isoquinoline radical, n is the number 1, 2, 3 or 4, if n is 1, A is $C_1$–$C_{30}$alkyl which is uninterrupted or interrupted by O, S or NH, $C_2$–$C_{12}$alkenyl, unsubstituted or $C_1$–$C_4$alkyl-substituted $C_5$–$C_{12}$cycloalkyl, benzyl, unsubstituted or $C_1$–$C_{18}$alkyl-substituted phenyl, a group $$-\left[CH_2-\underset{R_{19}}{CH}\right]_b-OH,$$

in which $R_{19}$ is hydrogen or methyl and b is a number from 1 to 10, or a radical

[bicyclic radical] or [bicyclic radical], if n is 2, A is $C_2$–$C_{18}$alkylene or $C_2$–$C_{18}$alkylene which is interrupted by —O—, —S— or —NH—, if n is 3, A is a group $$-CH_2-\underset{|}{CH}-CH_2-, \text{ and if n is 4, A is a group } C(CH_2)_{\overline{4}},$$

m is the number 1 or 2, in which, if m is 1, R' and R'', independently of one another, are hydrogen, $C_1$–$C_{18}$alkyl which is uninterrupted or interrupted by O, S or NH, $C_2$–$C_{12}$alkenyl, unsubstituted or $C_1$–$C_4$alkyl-substituted $C_5$–$C_{12}$cycloalkyl, unsubstituted or $C_1$–$C_{18}$alkyl-substituted phenyl, benzyl or a group $$-CH_2-\underset{R_{19}}{CH}-Y-R_{20},$$

in which Y is —O— or —NH—, $R_{19}$ has the abovementioned meaning and $R_{20}$ is hydrogen, —CO—(C$_1$-C$_{18}$alkyl) or —CO—(C$_2$-C$_{12}$alkenyl), or R' is hydrogen and R" is C$_1$-C$_{12}$alkoxy, a group

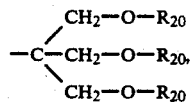

in which R$_{20}$ is as defined above, or a group

in which R$_{21}$ and R$_{22}$, independently of one another, are hydrogen, C$_1$-C$_{18}$alkyl, C$_2$-C$_{12}$alkenyl, unsubstituted or C$_1$-C$_{18}$alkyl-substituted phenyl, —CO—(C$_1$-C$_{18}$alkyl) or —CO—(C$_2$-C$_{12}$alkenyl), benzoyl or together a group =CH—R$_{23}$, in which R$_{23}$ is hydrogen, C$_1$-C$_{18}$alkyl, C$_2$-C$_{12}$alkenyl, C$_5$-C$_{12}$cycloalkyl or phenyl, or R' and R" together with the nitrogen atom to which they are bound form a pyrrolidine, imidazolidine, piperidine, piperazine or morpholine radical, and if m is 2, R' is hydrogen and R" is C$_2$-C$_{18}$alkylene.

Preference is given to compounds of the formulae

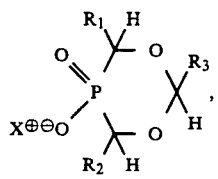 (IV)

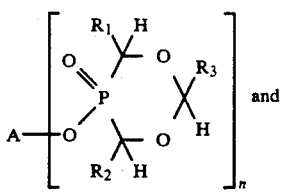 (V)

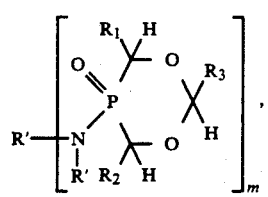 (VI)

in which
R$_1$, R$_2$ and R$_3$ are identical and are as defined above,
X$^\oplus$ is H$^\oplus$ or a group of the formulae (M$^{r\oplus}$/r) or N$^\oplus$(R$_{15}$)(R$_{16}$)(R$_{17}$)(R$_{18}$), in which M$^{r\oplus}$ is a mono- or divalent metal cation and R$_{15}$, R$_{16}$, R$_{17}$, R$_{18}$, independently of one another, are hydrogen, C$_1$-C$_{12}$alkyl or cyclohexyl,
n is the number 1 or 2, if n is 1 A is C$_1$-C$_{18}$alkyl, cyclohexyl, unsubstituted or C$_1$-C$_4$alkyl-substituted phenyl or benzyl, if n is 2, A is C$_2$-C$_{12}$alkylene or C$_2$-C$_{12}$alkylene which is interrupted by —O—,
m is the number 1 or 2, in which, if m is 1,
R' and R", independently of one another, are hydrogen, C$_1$-C$_{18}$alkyl, cyclohexyl, phenyl, benzyl or hydroxy-C$_2$-C$_4$alkyl, or
R' is hydrogen and R" is amino, C$_1$-C$_6$alkoxy or a group

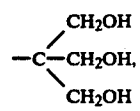

or R' and R" together with the N atom form a piperidine, piperazine or morpholine ring, and, if m is 2, R' is hydrogen and R" is C$_2$-C$_{18}$alkylene.

Particular preference is given to compounds of the formulae IV, V and VI in which R$_1$, R$_2$ and R$_3$ are identical and are a group —(CH$_2$)$_2$R$_7$, R$_7$ is a group —S—(C$_1$-C$_{14}$alkyl),

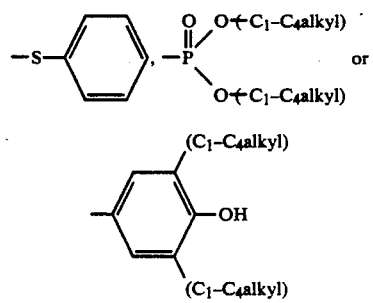

and R$_4$, R$_5$ and R$_6$ are hydrogen, X$^\oplus$ is H$^\oplus$, Na$^\oplus$, K$^\oplus$, Ca$^{2\oplus}$/2, Mg$^{2\oplus}$/2, Zn$^{2\oplus}$/2, Cu$^{2\oplus}$/2 or Ni$^{2\oplus}$/2, n is 1, A is C$_1$-C$_{18}$alkyl, m is 1, R' is hydrogen and R" is C$_1$-C$_4$alkyl, —CH$_2$—CH$_2$OH or —NH$_2$.

The invention also relates to the use of compounds of the formulae I, II and/or III for stabilising organic polymers, lubricants, metal-working fluids and hydraulic fluids against oxidative, thermal and/or actinic degradation, and as wear-resistant agents and high-pressure additives in lubricants.

The invention also comprises a process for stabilising organic polymers, lubricants, metal-working fluids and hydraulic fluids against oxidative, thermal and/or actinic degradation, which comprises adding at least one compound of the formulae I, II or III to these materials or applying it thereto as stabiliser.

The compounds according to the invention and the further dioxaphosphorinane compounds used in the compositions according to the invention are prepared by methods known per se, for example by the process described in U.S. Pat. Nos. 3,328,319 and 2,984,551, which can be summarised by the following reaction scheme:

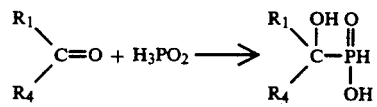

-continued

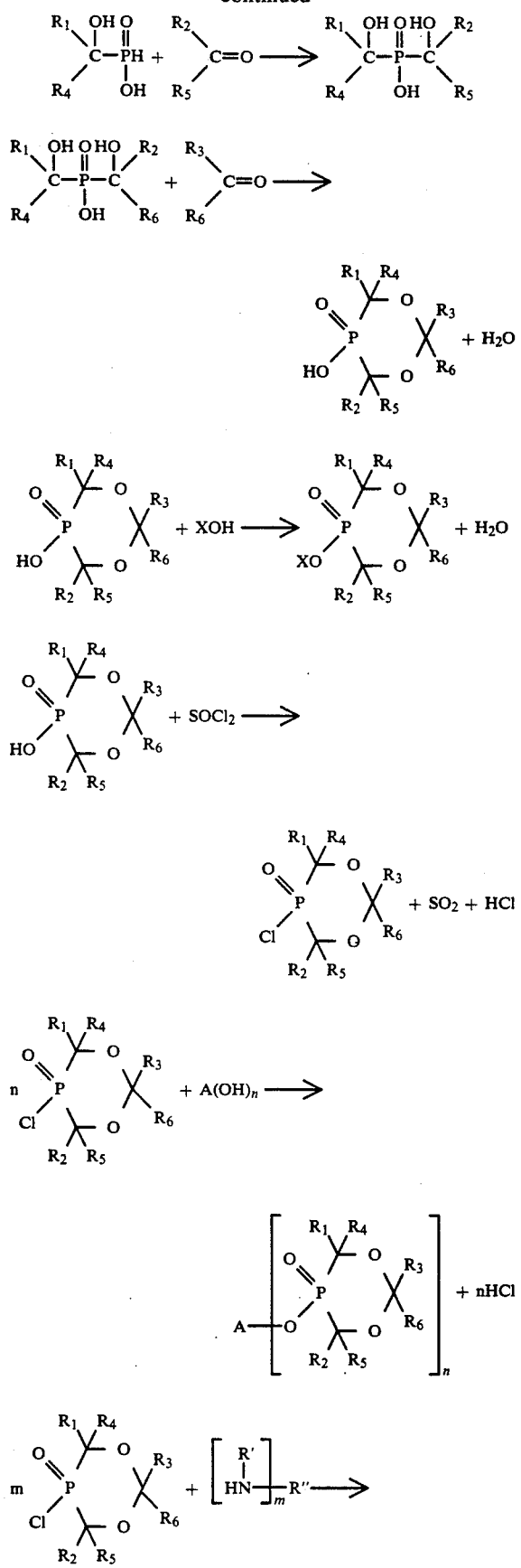

-continued

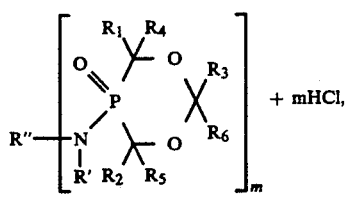

in which the substituents $R_1$, $R_2$, $R_3$, $R_4$, $R_5$, $R_6$, X, A, R' and R" and the symbols m and n are in each case as defined above.

The reactions are advantageously carried out under the same reaction conditions as described in the above-mentioned U.S. patents.

The free symmetrical 1,3,5-dioxaphosphorinane-5-hydroxy-5-oxides are in general available, for example, by (i.e. compounds of formula I in which $X^\oplus$ is $H^\oplus$, $R_4$, $R_5$ and $R_6$ are H and $R_1$, $R_2$ and $R_3$ have the same meaning) simple boiling of the corresponding aldehyde with aqueous hypophosphorous acid in toluene in a water separator according to the equation

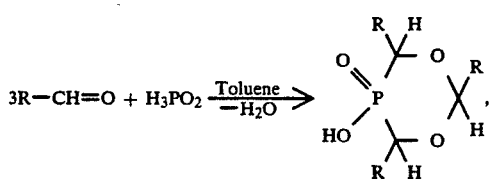

in which R has one of the meanings given for $R_1$, $R_2$ and $R_3$.

The salts of the 1,3,5-dioxaphosphorinane-5-hydroxy-5-oxides are advantageously prepared by neutralisation of the latter with the corresponding metal hydroxides or amines.

The esters, amides and hydrazides of the 1,3,5-dioxaphosphorinane 2,5-hydroxy-5-oxides can be prepared by reacting the corresponding easily accessible acid chlorides with alcohols, amines or hydrazines.

Some of the preparation processes described are illustrated in detail in the examples which follow.

The starting compounds required for the preparation processes described above are known or can be prepared in a manner known per se using customary methods.

The examples which follow illustrate the invention. Unless stated otherwise, the percentages given are by weight.

EXAMPLE 1

372 g (5.0 mol) of isobutyraldehyde and 220 g (1.667 mol) of hypophosphorous acid are heated to reflux under nitrogen in 500 ml of toluene in a water separator with stirring. After 6 hours, 139.45 g of water have been separated off. The toluene is distilled off at an oil bath temperature of 150° C., and the residue is dissolved in 1 l of acetonitrile. The resulting solution is refluxed for a short time and then poured into a wide neck 2 l Erlenmeyer flask. For crystallisation, the Erlenmeyer flask is placed in ice and its contents are thoroughly stirred until its temperature has reached ~0° C. The precipitated white crystals are filtered off with suction, washed with 400 ml of cold (0° C.) acetonitrile and dried in a vacuum drying cabinet at 60° C. for 15 hours, giving 375.75 (85.3% of theory) of the snow-white readily flowable compound 1 (Table I) of melting point 110°-130° C.

EXAMPLE 2

18.43 g (0.1 mol) of lauraldehyde and 4.40 g (0.033 mol) of 50% aqueous $H_3PO_2$ solution are boiled in 100 ml of toluene under argon in a water separator. After 4 hours, 2.7 ml of water have been separated off. The toluene is evaporated off in a rotary evaporator, and the residue is dissolved in 150 ml of ethanol. The thick crystalline paste formed after cooling to 0° C. is diluted with 100 ml of acetonitrile, filtered off with suction and washed with acetonitrile. A repeated crystallisation in the same manner using a small amount of activated carbon gives 16 g (79.9% of theory) of the colourless compound 12 (Table I) of melting point 60°-63° C.

EXAMPLE 3

3.86 g (0.05 mol) of calcium hydroxide are suspended in 5 ml of distilled water, and 100 ml of ethanol and 26.43 g (0.1 mol) of compound 1 (Table I) are then added. The mixture is stirred, during which almost everything goes into solution in a slightly exothermic reaction. After standing overnight, the reaction mixture is filtered and then freed of alcohol in a rotary evaporator. The white solid residue is then dried at 80° C./0.1 mbar for 3 hours, giving 26.84 g (95% of theory) of compound 16 (Table I); melting point >250° C.

EXAMPLE 4

13.2 g of compound 1 (Table I) are dissolved in 40 ml of methylene chloride, 10 ml of thionyl chloride and 3 drops of dimethylformamide are added, and stirring of the mixture at 50° C. is continued until no more evolution of gas takes place. The solvent is then distilled off in vacuo, and the residue is dried at 80° C./0.1 mbar for 30 minutes.

40 ml of methylene chloride are then added and then 10.9 ml of butylamine are added dropwise. After standing overnight, the reaction mixture is washed with water, dilute HCl and $NaHCO_3$ and dried over $MgSO_4$. The solvent is evaporated off, and the residue is recrystallised from petroleum ether, giving 10.2 g (55% of theory) of the white compound 5 (Table I) of melting point 137°-160° C. (mixture of isomers).

All dioxaphosphorinane compounds listed in Table I below and not yet mentioned in Examples 1 to 4 were prepared by the methods mentioned in Examples 1–4 from the corresponding known starting materials.

TABLE I

| No. | Compound | M.p. °C. | Analysis | | | |
|---|---|---|---|---|---|---|
| | | | | C | H | N | P |
| 1 | (structure: dioxaphosphorinane with HO–P, CH(CH$_3$)$_2$ substituents) | 110–130 | calc. found | 54.53 54.45 | 9.53 9.52 | — — | * * |
| 2 | (structure: HO(CH$_2$)$_2$HN–P, CH(CH$_3$)$_2$ substituents) | 145–155 | calc. found | 54.71 54.46 | 9.84 9.75 | 4.56 4.42 | * * |
| 3 | (structure: H$_2$N—HN–P, CH(CH$_3$)$_2$ substituents) | 180–185 | calc. found | 51.78 51.66 | 9.78 9.62 | 10.06 9.93 | * * |
| 4 | (structure: C$_4$H$_9$NH$_3^⊕$ O$^⊖$–P, CH(CH$_3$)$_2$ substituents) | 163–170 | calc. found | 56.95 56.91 | 01.75 10.76 | 4.15 4.06 | * * |
| 5 | (structure: C$_4$H$_9$HN–P, CH(CH$_3$)$_2$ substituents) | 137–160 | calc. found | 60.16 60.15 | 10.73 10.67 | 4.38 4.40 | * * |

TABLE I-continued

| No. | Compound | M.p. °C. | Analysis C H N P |
|---|---|---|---|
| 6 | (structure: phosphonate with H/CH(CH₃)₂ groups, CH₃O-P) | 46–48 | Structure confirmed by ¹H NMR |
| 7 | (structure: phosphonate with H/CH(CH₃)₂ groups, K⊕⊖O-P) | >300 | Structure confirmed by ¹H NMR |
| 8 | (structure: phosphonate with H/C(CH₃)₂ groups, HO-P) | 182–186 | calc. 58.80 10.20 — *<br>found 58.65 10.10 — * |
| 9 | (structure: phosphonate with H/C(CH₃)₂ groups, K⊕⊖O-P) | >300° C. | Structure confirmed by ¹H NMR |
| 10 | (structure: phosphonate with H/R groups, HO-P)<br>R = —C(H)(C₂H₅)(C₄H₉) | Oil | Structure confirmed by ¹H NMR |
| 11 | (structure: phosphonate with H/R groups, K⊕⊖O-P)<br>R = —C(H)(C₂H₅)(C₄H₉) | Resin | Structure confirmed by ¹H NMR |
| 12 | (structure: phosphonate with H/C₁₁H₂₃ groups, HO-P) | 60–63 | calc. 71.95 12.24 — 5.15<br>found 71.96 12.22 — 5.19 |

TABLE I-continued

| No. | Compound | M.p. °C. | Analysis | | | |
|---|---|---|---|---|---|---|
| | | | C | H | N | P |
| 13 | [structure with HC₁₁H₂₃ groups, K⁺ salt] | 210–240 | Structure confirmed by ¹H NMR | | | |
| 14 | [structure, HO–P, R = −(CH₂)₂S−C₁₂H₂₅] | 70–75 | calc. 65.64 found 65.58 | 11.14 11.14 | — — | * * |
| 15 | [structure with cyclohexenyl groups, HO–P] | 185–205 | calc. 66.65 found 66.65 | 8.26 8.15 | — — | * * |
| 16 | [structure with CH(CH₃)₂ groups, Ca²⁺/2 salt] | >250° | calc. 50.87 found 50.93 | 8.54 8.56 | — — | * * |
| 17 | [structure, HO–P, R = −(CH₂)₂P(O)(OC₄H₉)₂] | Oil | Structure confirmed by ¹H NMR | | | |
| 18 | [structure, HO–P] | 180–90° | calc. 73.35 found 73.20 | 9.53 9.54 | — — | * * |

TABLE I-continued

| No. | Compound | M.p. °C. | Analysis | | | |
|---|---|---|---|---|---|---|
| | | | C | H | N | P |

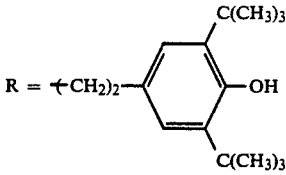

*not determined
Compounds 8, 10, 14, 17 and 18 are prepared in analogy to Example 1, compounds 4, 7, 9, 11, 13 and 16 in analogy to Example 3 and compounds 2, 3, 5 and 6* in analogy to Example 4.
**Addition of the amine instead of the hydroxide
***Addition of CH₃OH instead of amine.

The compounds listed in Table II are obtained analogously to Examples 3 and 4.

TABLE II

| No. | Compound | M.p. °C. | Analysis | | |
|---|---|---|---|---|---|
| | | | C | H | N |
| 19 | 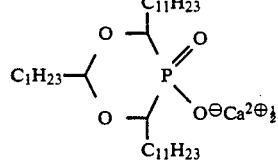 | Resin | Determination of Ca: Calculated Ca: 3,23% Found Ca: 3,22% | | |
| 20 | 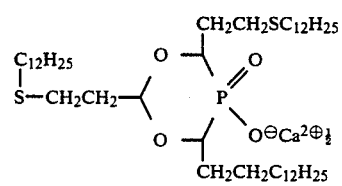 | Resin | Determination of Ca: Calculated Ca: 2.38% Found Ca: 2.37% | | |
| 21 | 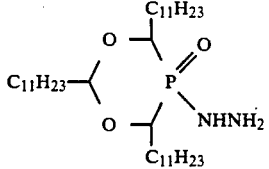 | 53–59 | calc. 70.31 found 70.24 | 12.29 12.11 | — — |
| 22 | 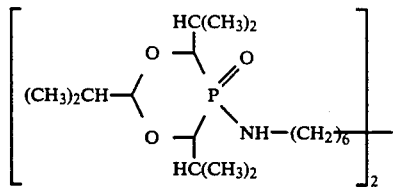 | 170–180 | calc. 62.40 found 62.47 | 10.76 10.76 | — — |
| 23 | 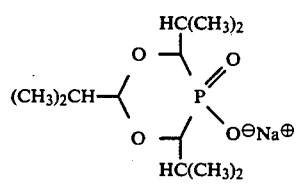 | >250° C. | calc. 50.35 found 50.13 | 8.45 8.51 | — — |
| 24 | 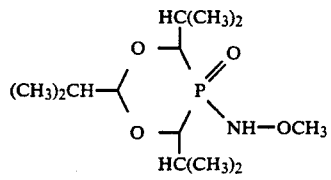 | 115–145 | calc. 53.23 found 53.32 | 9.62 9.68 | 4.77 4.50 |

TABLE II-continued

| No. | Compound | M.p. °C. | Analysis | | |
|-----|----------|----------|---|---|---|
| | | | C | H | N |
| 25 | (structure: dioxaphosphorinane with HC(CH₃)₂ groups, (CH₃)₂CH—, P=O, N-piperidine) | Oil | calc. 61.61 found 61.46 | 10.34 10.48 | 4.23 4.16 |
| 26 | (structure: bis-dioxaphosphorinane with HC(CH₃)₂ groups, (CH₃)₂CH—, P=O, O—CH₂CH₂—O linker, subscript 2) | Oil | calc. 56.17 found 56.04 | 9.43 9.70 | — — |

Compounds 19, 20 and 23 are prepared in analogy to Example 3, compounds 21, 22, 24, 25 and 26* in analogy to Example 4.

*Addition of alcohol instead of amine.

EXAMPLE 5

Stabilisation of SBS against crosslinking during Brabender ageing 0.4% of compound 1 (Table I) are added in a Brabender mixer to a thermoplastic SBS elastomer (®Finaprene 416). During the Brabender ageing at 200° C., 60 rpm, the specimen thus stabilised has an induction time of 23 minutes until crosslinking (increase in torque) is observed. Without the addition of 1, crosslinking takes place after as little as 4 minutes.

EXAMPLE 6

Stabilisation of polypropylene against discolorations during processing 1.3 kg of polypropylene powder are mixed with 0.05% tris(2,4-di-tert-butylphenyl)phosphite, 0.05% of tetrakis[3,5-di-tert-butyl-4-hydroxyphenylpropionyloxymethyl]methane, 0.05% of calcium stearate and the stabilisers listed in Table III. This mixture is extruded in an extruder having a cylinder diameter of 20 mm and a length of 400 mm at 100 revolutions per minute, in which 3 heating zones are set 260° C., to 270° C. and 280° C. For cooling, the extrudate is led through a water bath and then granulated. The granules obtained are extruded 3 times. After the third extrusion, a 2 mm pressed sheet on which the Yellowness Index YI is measured according to ASTM D-1925-70 is made from the granules. Low YI values denote little discoloration and high YI values stronger discoloration of the sheets. For the results, see Table III.

TABLE III

Yellowness Indices YI of PP pressed sheets (2 mm) after multiple extrusion at 280° C. Polymer: ® Propathene HF20.
Basis stabilisation:
0.05% of tetrakis[3,5-di-tert-butyl-4-hydroxyphenylpropionyl-oxymethyl]methane
+0.05% of calcium stearate
+0.05% of tris(2,4-di-tert-butylphenyl) phosphite

| Formulation | YI after 3rd extrusion |
|---|---|
| Basis | 4.2 |
| +0.05% Compound 1 from Table I | 2.8 |
| +0.05% Compound 16 from Table I | 2.7 |
| +0.025% Compound 3 from Table I | 1.9 |
| +0.05% Compound 15 from Table I | 2.5 |

TABLE III-continued

Yellowness Indices YI of PP pressed sheets (2 mm) after multiple extrusion at 280° C. Polymer: ® Propathene HF20.
Basis stabilisation:
0.05% of tetrakis[3,5-di-tert-butyl-4-hydroxyphenylpropionyl-oxymethyl]methane
+0.05% of calcium stearate
+0.05% of tris(2,4-di-tert-butylphenyl) phosphite

| Formulation | YI after 3rd extrusion |
|---|---|
| +0.05% Compound 5 from Table I | 1.9 |
| +0.05% Compound 23 from Table II | 2.1 |

EXAMPLE 7

Use in lubricant

Test for wear resistance

For testing the suitability as wear-resistant additive, the ASTM standard method D-2783-81 using the Shell four-ball tester is employed. The basis oil used is ®Mobil BB from Shell. The following properties are determined:

a) the weld load WL as the load (in kg) at which the 4 balls are welded together within 10 seconds, and
b) the average wear scar diameter at a load of 20 kg over a period of 1 hour (in mm).

| Compound (Table) | Amt. of additive (% by wt.) | Weld Load (kg) | Wear Scar Diameter (mm) |
|---|---|---|---|
| — | — | 1300 | 0.82 |
| 10 | 0.25 | — | 0.37 |
| | 1.0 | 1600 | 0.31 |
| 12 | 0.25 | — | 0.33 |
| | 1.0 | 1600 | 0.33 |
| 14 | 0.25 | — | 0.37 |
| | 1.0 | 1600 | 0.41 |

What is claimed is:

1. A composition comprising (a) an organic polymer, with the exception of polymers based on epoxy resin, a lubricant, a metal-working fluid or a hydraulic fluid and (b) 0.001 to 10% by weight, relevant to (a), at least one dioxaphosphorinane compound of the formulae

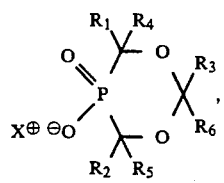 (I)

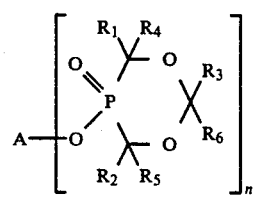 (II)

or/and

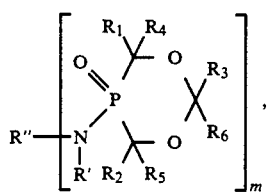 (III)

in which $R_1$, $R_2$, $R_3$, $R_4$, $R_5$ and $R_6$, independently of one another, are hydrogen, $C_1$–$C_{18}$alkyl which is uninterrupted or interrupted by O, S or NH, $C_2$–$C_{12}$alkenyl, unsubstituted or $C_1$–$C_4$-alkyl-substituted $C_5$–$C_{12}$cycloalkyl, cyclohexenyl, phenyl, which is unsubstituted or substituted with $C_1$–$C_{18}$alkyl, hydroxyl, $C_1$–$C_{18}$alkoxy, $C_2$–$C_{18}$alkoxycarbonyl or-/and $C_1$–$C_{18}$alkylmercapto, or are a group

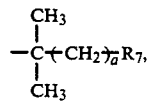

in which a is zero or one and $R_7$ is

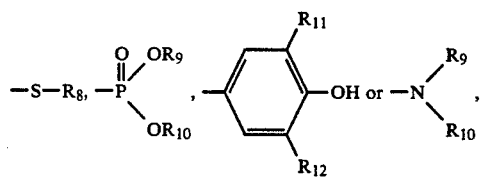

$R_8$ is $C_1$–$C_{18}$alkyl, $C_2$–$C_{12}$alkenyl, phenyl, benzyl or $-CH_2-COOR_{13}$, $R_9$ and $R_{10}$, independently of one another, are hydrogen, $C_1$–$C_{18}$alkyl, $C_5$–$C_{12}$cycloalkyl or phenyl, $R_{11}$ and $R_{12}$, independently of one another, are hydrogen, $C_1$–$C_4$alkyl, cyclohexyl or phenyl, $R_{13}$ is hydrogen, $C_1$–$C_{18}$alkyl, $C_2$–$C_{12}$alkenyl, $C_5$–$C_{12}$cycloalkyl or benzyl, or $R_1$, $R_2$, $R_3$, $R_4$, $R_5$ and $R_6$, independently of one another, are a group $-COOR_{13}$,

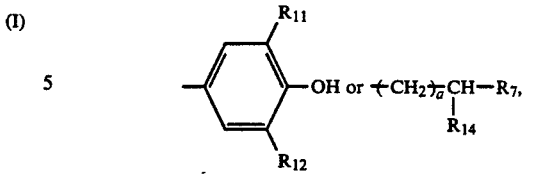

in which $R_7$, $R_{11}$, $R_{12}$, $R_{13}$ and a have the abovementioned meaning and $R_{14}$ is hydrogen if a is zero and is hydrogen, methyl or phenyl if a is 1, $X^\oplus$ is $H^\oplus$ or a group of the formulae ($M^{r\oplus}/r$) or $N^\oplus(R_{15})(R_{16})(R_{17})(R_{18})$, in which $M^{r\oplus}$ is an r-valent metal cation, r is the number 1, 2 or 3, $R_{15}$, $R_{16}$, $R_{17}$, $R_{18}$, independently of one another, are hydrogen, $C_1$–$C_{18}$alkyl, $C_5$–$C_{12}$cycloalkyl, unsubstituted or $C_1$–$C_{18}$alkyl-substituted phenyl or $R_{17}$ and $R_{18}$ together with the N atom form a pyrrolidine, imidazolidine, piperidine, piperazine or morpholine radical, or $R_{16}$, $R_{17}$ and $R_{18}$ together with the N atom form a pyridine, picoline, pyrazine, quinoline or isoquinoline radical, n is the number 1, 2, 3 or 4, if n is 1, A is $C_1$–$C_{30}$alkyl which is uninterrupted or interrupted by O, S or NH, $C_2$–$C_{12}$alkenyl, unsubstituted or $C_1$–$C_4$alkyl-substituted $C_5$–$C_{12}$cycloalkyl, benzyl, unsubstituted or $C_1$–$C_{18}$alkyl-substituted phenyl, a group

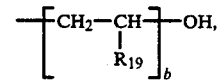

in which $R_{19}$ is hydrogen or methyl and b is a number from 1 to 10, or a radical

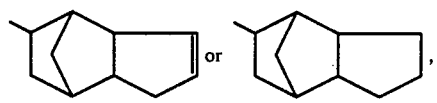

if n is 2, A is $C_2$–$C_{18}$alkylene or $C_2$–$C_{18}$alkylene which is interrupted by —O—, —NH— or —S—, if n is 3, A is a group —$CH_2$—$CH$—$CH_2$—, and if n is 4, A is a group $C(CH_2)_4$, m is the number 1 or 2, in which, if m is 1, R' and R'', independently of one another, are hydrogen, $C_1$–$C_{18}$alkyl which is uninterrupted or interrupted by O, S or NH, $C_2$–$C_{12}$alkenyl, unsubstituted or $C_1$–$C_4$alkyl-substituted $C_5$–$C_{12}$cycloalkyl, unsubstituted or $C_1$–$C_{18}$alkyl-substituted phenyl, benzyl or a group

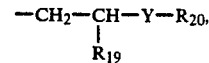

in which Y is —O— or —NH—, $R_{19}$ has the abovementioned meaning and $R_{20}$ is hydrogen, —CO—(C$_1$-C$_{18}$alkyl) or —CO—(C$_2$-C$_{12}$alkenyl), or R' is hydrogen and R" is C$_1$-C$_{12}$alkoxy, a group

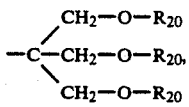

in which R$_{20}$ is as defined above, or a group

in which R$_{21}$ and R$_{22}$, independently of one another, are hydrogen, C$_1$-C$_{18}$alkyl, C$_2$-C$_{12}$alkenyl, unsubstituted or C$_1$-C$_{18}$alkyl-substituted phenyl, —CO—(C$_1$-C$_{18}$alkyl) or —CO—(C$_2$-C$_{12}$alkenyl), benzoyl or together a group =CH—R$_{23}$, in which R$_{23}$ is hydrogen, C$_1$-C$_{18}$alkyl, C$_2$-C$_{12}$alkenyl, C$_5$-C$_{12}$cycloalkyl or phenyl, or R' and R" together with the nitrogen atom to which they are bound form a pyrrolidine, imidazolidine, piperidine, piperazine or morpholine radical, and if m is 2, R' is hydrogen and R" is C$_2$-C$_{18}$alkylene.

2. A composition as claimed in claim 1, wherein R$_1$, R$_2$ and R$_3$ in the dioxaphosphorinane compounds of the formulae I, II and III are identical and are as defined in claim 1 and R$_4$, R$_5$ and R$_6$ are hydrogen.

3. A composition as claimed in claim 1, wherein R$_1$, R$_2$ and R$_3$ in the dioxaphosphorinane compounds of the formulae I, II and III are identical and are C$_1$-C$_{18}$alkyl, cyclohexyl, cyclohexenyl or a group —(CH$_2$)$_n$R$_7$, R$_7$ is a group —S—(C$_1$-C$_{18}$alkyl),

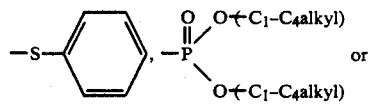

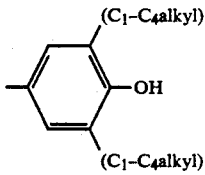

and R$_4$, R$_5$ and R$_6$ are hydrogen.

4. A composition as claimed in claim 2, wherein in the dioxaphosphorinane compounds of the formulae I, II and III X$^\oplus$ is H$^\oplus$ or a group of the formulae (M$^{r\oplus}$/r) or N$^\oplus$(R$_{15}$)(R$_{16}$)(R$_{17}$)(R$_{18}$), in which M$^{r\oplus}$ is a mono- or divalent metal cation and R$_{15}$, R$_{16}$, R$_{17}$, R$_{18}$, independently of one another, are hydrogen, C$_1$-C$_{12}$alkyl or cyclohexyl, n is the number 1 or 2, if n is 1, A is C$_1$-C$_{18}$alkyl, cyclohexyl, unsubstituted or C$_1$-C$_4$alkyl-substituted phenyl or benzyl, if n is 2, A is C$_2$-C$_{12}$alkylene or C$_2$-C$_{12}$alkylene which is interrupted by —O— or —S—, m is the number 1 or 2, in which, if m is 1, R' and R" independently of one another, are hydrogen, C$_1$-C$_{18}$alkyl, cyclohexyl, phenyl, benzyl or hydroxy-C$_1$-C$_4$alkyl, or R' is hydrogen and R" is amino, C$_1$-C$_6$alkylamino, C$_2$-C$_{12}$dialkylamino, C$_1$-C$_6$alkoxy or a group

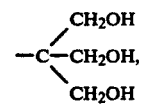

or R' and R" together with the N atom form a piperidine, piperazine or morpholine ring and, if m is 2, R' is hydrogen and R" is C$_2$-C$_{18}$alkylene.

5. A composition as claimed in claim 1, wherein in the dioxaphosphorinane compounds of the formulae I, II and III X$^\oplus$ is H$^\oplus$, Na$^\oplus$, K$^\oplus$, Ca$^{2\oplus}$/2, Mg$^{2\oplus}$/2, Zn$^{2\oplus}$/2, Cu$^{2\oplus}$/2, Ni$^{2\oplus}$/2, or $^\oplus$N(R$_{15}$)(R$_{16}$)(R$_{17}$)(R$_{18}$) and R$_{15}$, R$_{16}$, R$_{17}$ and R$_{18}$, independently of one another, are hydrogen or C$_1$-C$_6$alkyl, n is the number 1 or 2, A is C$_1$-C$_{12}$alkyl, if n is 1, and C$_2$-C$_{12}$alkylene or C$_2$-C$_{12}$alkylene which is interrupted by —O—, if n is 2 m is the number 1 or 2, in which, if m is 1,

R' and R", independently of one another, are hydrogen, C$_1$-C$_6$alkyl, hydroxy-C$_2$-C$_4$alkyl, or R' is hydrogen and R" is amino or C$_1$-C$_4$alkoxy, or R' and R" together with the N atom form a piperidine, piperazine or morpholine radical, if m is 2, R' is hydrogen and R" is C$_2$-C$_{18}$alkylene, R$_1$, R$_2$ and R$_3$ are identical and C$_1$-C$_{12}$alkyl, cyclohexenyl or a group of the formula —(CH$_2$)$_2$—R$_7$, in which R$_7$ is —S—C$_1$-C$_{14}$alkyl,

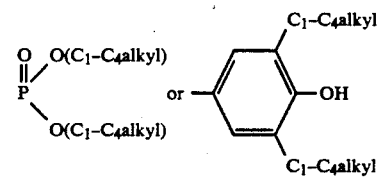

and R$_4$, R$_5$ and R$_6$ are hydrogen.

6. A composition as claimed in claim 4, wherein in the dioxaphosphorinane compounds of the formulae I, II and III X$^\oplus$ is H$^\oplus$, Na$^\oplus$, K$^\oplus$, Ca$^{2\oplus}$/2, Mg$^{2\oplus}$/2, Zn$^{2\oplus}$/2, Cu$^{2\oplus}$/2 or Ni$^{2\oplus}$/2, A is C$_1$-C$_{18}$alkyl, phenyl, benzyl, C$_2$-C$_{12}$alkylene or C$_2$-C$_{12}$alkylene which is interrupted by —O— or —S—, R' and R", independently of one another, are hydrogen, C$_1$-C$_{12}$alkyl, phenyl, benzyl or hydroxyl-C$_2$-C$_4$alkyl or R' is hydrogen and R" is C$_1$-C$_4$alkoxy, amino or C$_2$-C$_{18}$alkylene, or R' and R" together with the N atom form a piperidine, piperazine or morpholine radical.

7. A composition as claimed in claim 1, comprising an organic polymer and at least one dioxaphosphorinane compound of the formulae I, II or III.

8. A composition as claimed in claim 7, in which the organic polymer is a thermoplastic or an elastomer.

9. A composition as claimed in claim 7, in which the organic polymer is a polyolefin.

10. A composition as claimed in claim 1, comprising a lubricant, a metal-working fluid or a hydraulic fluid and at least one dioxaphosphorinane compound of the formulae I, II or III.

11. A composition as claimed in claim 1, comprising a lubricant and a dioxaphosphorinane compound of the formulae I, II or III.

12. A composition as claimed in claim 1, additionally comprising further stabilizers, selected from the group consisting of antioxidants, light stabilizers and processing stabilizers.

13. A process for stabilising organic polymers, lubricants, metal-working fluids and hydraulic fluids against oxidative, thermal and/or actinic degradation, which comprises adding at least one compound of the formula I, II or III according to claim 1 to these materials or applying it thereto as stabiliser.

14. A composition according to claim 1 wherein (b) is 0.01 to 5% by weight, relevant to (a).

15. A composition according to claim 14 wherein (b) is 0.1 to 2% by weight, relevant to (a).

* * * * *